United States Patent [19]

Jones, Sr.

[11] 4,040,423
[45] Aug. 9, 1977

[54] URINE TRAP DIAPER

[76] Inventor: John Leslie Jones, Sr., 1070 Glen Oaks Blvd., Pasadena, Calif. 91105

[21] Appl. No.: 706,761

[22] Filed: July 23, 1976

[51] Int. Cl.² ............... A61F 13/16; A61F 13/18
[52] U.S. Cl. .................. 128/287; 128/284; 128/290 P; 128/290 R; 128/296
[58] Field of Search ............ 128/284, 287, 290 R, 128/290 P, 296

[56] References Cited
U.S. PATENT DOCUMENTS

| 2,788,003 | 4/1957 | Morin | 128/284 |
|---|---|---|---|
| 2,895,477 | 7/1959 | Bernard | 128/284 |
| 3,211,147 | 10/1965 | Pherson et al. | 128/284 |
| 3,481,337 | 12/1969 | Ruffo | 128/284 |
| 3,650,273 | 3/1972 | Schaar | 128/287 |
| 3,658,063 | 4/1972 | Schaar | 128/287 |
| 3,731,688 | 5/1973 | Litt | 128/287 |
| 3,765,418 | 10/1973 | Jones, Sr. | 128/287 |
| 3,968,798 | 7/1976 | Hokanson | 128/284 |

Primary Examiner—Aldrich F. Medbery
Attorney, Agent, or Firm—J. L. Jones, Sr.

[57] ABSTRACT

In an infant disposable diaper the absorbent diaper pad for body excreta has a pair of narrow width pleats disposed in the absorbent pad. Each one of the pleats being oppositely disposed parallel along the full longitudinal length of the diaper pad, the pair of pleats being separated by a suitable width of absorbent pad, providing a central pad channel width as a urine and feces trap and an excreta channel pad area suitable for containment of excreta between the pleat pair. Each one of the pad pleats can be formed of the central optimum pad area and each pleat is disposed on the exterior first face of the diaper pad. Each pleat is disposed adjacent to the longitudinal exterior margin of the central pad area. A thin, flexible, fluid impermeable membrane is contiguously disposed coextensive with the second face of the diaper pad area. The impermeable membrane is specifically excluded from contact with the side width values of the pair of narrow width pleat sides. The membrane is fixed in position and secured to the pad by at least a pair of opposed longitudinal border seals.

12 Claims, 6 Drawing Figures

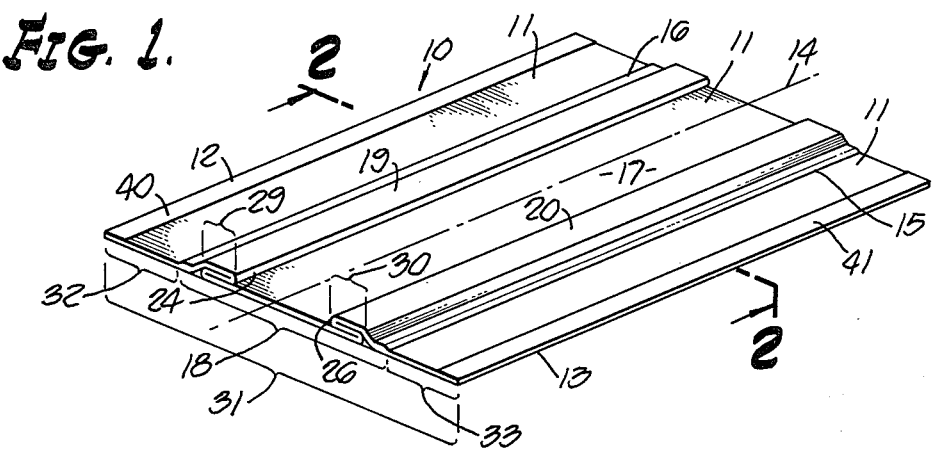
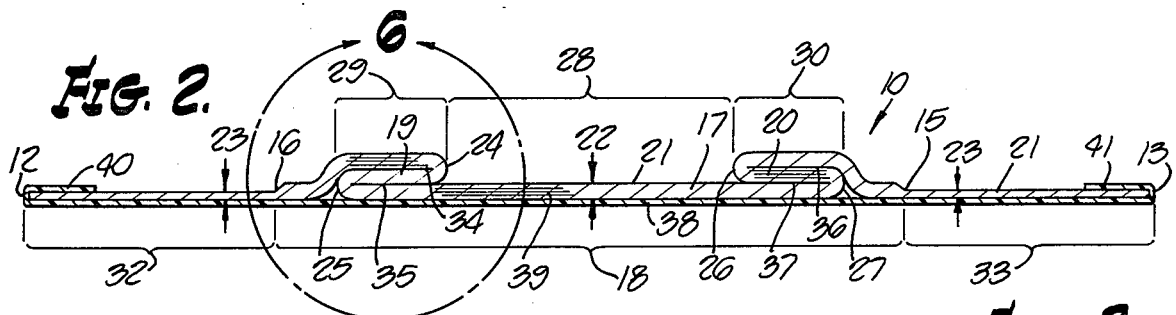
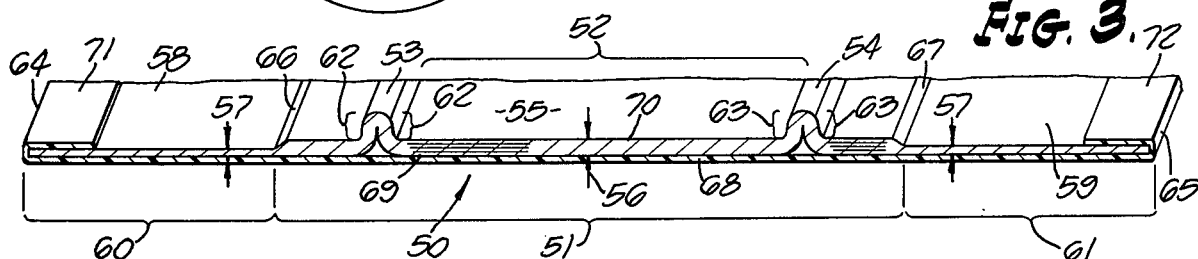
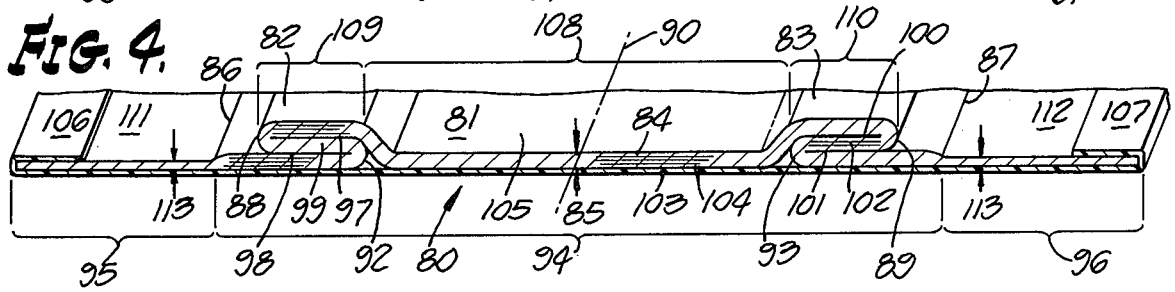
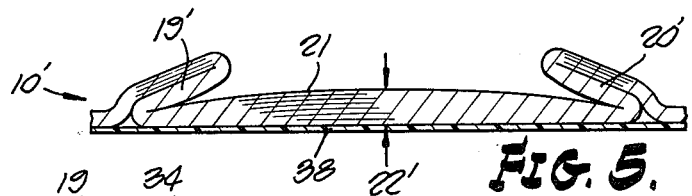
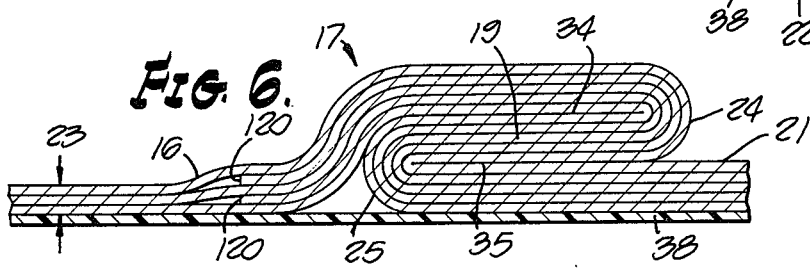

URINE TRAP DIAPER

CROSS REFERENCE TO A RELATED APPLICATION

This application is related by being directed to the same field of invention, to another application filed this same date as, Ser. No. 706,762, now U.S. Pat. No. 4,041,950 and titled FLUFFED PULP URINE TRAP DIAPER, by the same sole inventor, John Leslie Jones, Sr.

BACKGROUND OF THE INVENTION

The diaper of this invention is classified in Class 128, including the Sub-classes 287 and 284.

SUMMARY OF THE INVENTION

A rectangular infant diaper can have multiple plies of coplanar marginally aligned fluid absorbent paper sheet subgroups disposed in a pad area and a pair of longitudinally diaper pad exterior margins oppositely disposed to each other. The pad area has a central longitudinally diaper pad axis and a total diaper width axis normal to the longitudinal axis. Each one of the at least two subgroups of marginally aligned, plural fluid absorbent paper sheet pad areas have one longitudinal margin serially coincident with one of the two longitudinal diaper pad exterior margins. Each one of the serial sub-group pad areas provide a substantial width overlap of the serially subsequent sub-group, forming a central optimum pad area having the required multiplicity of fluid absorbent paper sheets. A pair of narrow width pad pleats are oppositely disposed, each one of the pleats being parallel to the full longitudinal axis length of the diaper pad. Each one of the pair of pad pleats can be formed of optimum absorbent pad area, or each one of the pleats can be formed of absorbent pad area adjacent to but not in the optimum pad area. Each one of the pleats can be disposed in an absorbent pad of uniform pad thickness. Each one of the pleats are disposed on the first face of the absorbent pad adjacent to one longitudinal exterior margin of the central pad area. Each one of the pad pleats can be flat-folded, and alternatively can be free standing. The pleat apex of a flat-folded pleat can be disposed nearer to or further from the central longitudinal diaper pad axis than the companion pleat base fold. A substantial area proportion of the central pad area is free of coverage by the pair of pleats. A thin, flexible, urine impermeable membrane is disposed coextensive with the second face of the absorbent pad, opposite the pad first face having the pleats disposed thereon. The membrane is specifically free of coextensive contact with the side width values of the pair of pleats. The membrane does form a pair of opposed longitudinal border seals on the first face of the pair of longitudinal exterior diaper pad margins. The opposed pair of pleats formed adjacent to the channel pad area provide a pair of dikes or retaining walls, which effectively provide a channel correctly anatomically positioned to accept urine and feces excreta from the infant wearing the diaper, and to contain the urine for the few seconds before the urine is absorbed by the central pad area. The excreta channel pad area is a urine trap, controlling urine flow and preventing the soiling of the wearer's clothes, crib sheets, and the like.

Included in the objects of this invention are: To provide an optimum profile infant diaper having a paired pleat structure, providing an improved excreta channel paid area in an infant diaper, and providing a better urine trap.

To provide an infant disposable infant diaper having improved means for controlling urine absorption in the excreta channel pad area section of the absorbent pad.

To provide a disposable infant diaper suitable for securely disposing the infant diaper around the pair of infant thighs, preventing urine leakage from the urine trap.

To provide an infant disposable diaper adappting readily to fitting the daily increasing infant body size during this very rapid infant growth period, with effectiveness in trapping urine.

To provide an effective means of trapping infant urine in a disposable infant diaper.

Further objects and advantages of this invention will become apparent in the following description, to be read in conjunction with the accompanying drawing.

BRIEF DESCRIPTION OF THE DRAWINGS

FIG. 1 is a perspective plan view illustrating the general configuration of the infant diaper and the opposed pair of longitudinal narrow width, flat folded pleats disposed parallel in combination with the thin fluid impermeable membrane.

FIG. 2 is an elevational sectional view through 2—2 of FIG. 1.

FIG. 3 is a partial perspective and a sectional view of an infant diaper illustrating free-standing pleats in combination with the impermeable membrane of this invention.

FIG. 4 is another perspective and sectional view of an infant diaper, illustrating a parallel pair of flat folded pleated providing a pleat apex disposed further from the central longitudinal diaper pad axis than the corresponding pleat base fold.

FIG. 5 is a sectional view of another modification of this infant diaper invention wherein the folded pleats are formed of an absorbent pad having a uniform pad thickness, except in the thicker excreta channel pad area.

FIG. 6 is an enlarged fragmentary sectional view illustrating the detailed structure of the diaper pleat as shown in view 6 of FIG. 2.

DESCRIPTION OF THE PREFERRED EMBODIMENT

Referring to FIG. 1 in detail, the infant diaper 10, having a rectangular area, has a multiple ply, coplanar fluid absorbent paper sheet pad area 11. The diaper 10 has the pair of longitudinal diaper pad exterior margins 12 and 13, and a central longitudinal diaper pad axis 14. The total pad width axis 31 is normal to the central longitudinal diaper pad axis 14.

The disclosure and claims in my earilier U.S. Pat. No. 3,765,418 issued Oct. 16, 1973, are referenced with respect to the teachings of the optimum profile fluid absorbent diaper. The plural sub-groups of marginally aligned, fluid absorbent paper sheet pad areas form the absorbent pad area 11. The plural sub-groups pad areas each have one sub-group longitudinal pad margin coincident with one of the two diaper pad margins 12 and 13. Thus one sub-group has a width extending from diaper pad exterior margin 12 to the sub-group longitudinal margin 15, and the second sub-group has a width extending from the diaper pad longitudinal exterior margin 13 to the sub-group longitudinal margin 16, and the alternate serial sub-groups are spaced so forth.

Views of both FIGS. 1 and 2 together illustrate that the central optimum pad area 17 has a width 18 and a thickness 22 of plural sub-group pads, compared to the border sub-group pad thickness 23. The central optimum pad area 17 has a pair of narrow width pad pleats 19 and 20 disposed parallel to the full longitudinal diaper axis 14 length. Each one of the pad pleats 19 and 20 are formed of the material of the central pad area 17, and the narrow width pleats 19 and 20 are disposed on the first face 21 of the central pad area 17. The pleat 19 is disposed parallel and adjacent to the longitudinal exterior margin 16 of the central pad area 17, and the pleat 20 is disposed parallel and adjacent to the longitudinal exterior margin 15 of the central pad area 17. Each one of the narrow width pleats 19 and 20 are folded flat. Pleat 19 has a pleat apex 24 disposed nearer the central longitudinal axis 14 than the corresponding companion pleat base fold 25. Pleat 20 has a pleat apex 24 disposed nearer the central longitudinal axis 14 than the corresponding companion pleat base fold 25. Pleat 20 has a pleat apex 26 disposed nearer the axis 14 than the corresponding pleat base fold 27. The central optimum pad area 17 has a central pad channel width 28 included in the central pad width 18. The channel width 28 is free of coverage by the pleats 19 and 20. The pleats 19 and 20, having pleat width 29 and 30, together with central pad width 28 together form the infant excreta channel pad area.

The pad area 11 has a total diaper pad width axis value 31 comprising the component width value 18 plus the two border width values 32 and 33. The diaper pad width axis value 31 specifically excludes the side width values 34 and 35 of pleat 19 and the side width values 36 and 37 of pleat 20.

The thin, flexible, fluid impermeable membrane 38 is disposed adjacently coextensive with the diaper pad width value 31 and with the second face 39 of the entire absorbent pad area 11 for the length of the longitudinal diaper axis 14. The membrane 38 is also folded over the exterior margins 12 and 13, forming a pair of opposed longitudinal border seals 40 and 41, sealed to pad area 11 in accordance with known teachings.

Referring to FIG. 3, the partial perspective and sectional view illustrates another modification of an infant diaper 50, having the general dimensions and the useful application of the diaper 10 of FIG. 1. The diaper 50 has the general equivalent of the plural sub-group of marginally aligned, fluid absorbent paper sheet construction of the diaper of FIG. 1. The central optimum pad width 51 of diaper 50 also includes the central pad channel width 52 which is free of coverage by the pair of freestanding pleats 53 and 54. The free-standing pleats 53 and 54 are formed of the central optimum pad area 55 having the absorbent pad thickness 56, which is substantially thicker than the thickness 57 of the two border longitudinal absorbent panels 58 and 59. The panels 58 and 59 have the respective panel widths 60 and 61. The diaper total paid width axis value includes the central optimum pad width 51 plus the border panel widths 60 and 61, and specifically excludes the side width values 62 and 63 of the respective free standing pleats 53 and 54.

The diaper 50 possesses the general structure of diaper 10, having a first and a second longitudinal diaper pad margin, 64 and 65 respectively, together with a first and second longitudinal margin 66 and 67 of the central optimum pad area 55. The thin, flexible, urine impermeable membrane 68 is disposed continuously adjacent over the total paid width axis to the second face 69 of the absorbent pad area. The membrane 68 is opposed to the open, first face 70 of the pad area 55. The membrane 68 has a width of 51 plus 60 and 61, together with the additional membrane width required to cover the longitudinal border margins 64 and 65, and to cover and form the respective two longitudinal border seals 71 and 72 in a known manner.

A still further modification of the diaper improvement is illustrated in FIG. 4, wherein a partial elevational and sectional view of infant diaper 80 is shown. The infant diaper 80 has overall rectangular dimensional configuration similar to diaper 10 of FIG. 1, together with the referenced multiple sub-group paper sheet pad area of U.S. Pat. No. 3,765,418. The central optimum pad area 81 has a pair of opposed narrow flat pleats 82 and 83 formed on the first pad face 84. The pleats 82 and 83 are formed of the central optimum pad area 81, which has the pad thickness 85. Each one of the pleats 82 and 83 are disposed the full diaper longitudinal pad length, like the pleats 19 and 20 in diaper 10, and each pleat 82 and 83 is disposed adjacent to the respective longitudinal sub-group pad exterior margins 86 and 87. The diaper 80 illustrates that the two narrow flat-folded pleat apexes 88 and 89, of the respective pleats 82 and 83, are disposed further from the central diaper longitudinal axis 90 than the respective corresponding two pleat base folds 92 and 93. The total diaper pad width value comprises the value of the central optimum pad width axis 94 and the two border pad widths 95 and 96 values, and specifically excludes the side width values 97 and 98 of pleat 99, and also excludes the side width values 100 and 101 of pleat 102. The thin, flexible, urine fluid impermeable membrane 103 is disposed contiguously adjacent the second face 104 of the diaper absorbent pad 105, as in diapers 10 and 50. The pair of opposed longitudinal border seals 106 and 107 extend the full length of the longitudinal diaper axis, as in diaper 10, and are formed by overlapping the membrane 103 over the total diaper paid width value and sealing the border seals 106 and 107 in a known manner to the pad 105. The central optimum pad area 81 has a channel pad width 108 free of coverage by the pair of pleat widths 109 and 110. The channel paid width 108, together with pleats 99 and 102 together provided an excreta channel pad area. Two border pad widths 95 and 96 partially define the two absorbent pads 111 and 112 disposed one on each side of the central optimum pad area 81 over the complete diaper length, as in diaper 10. The pads 111 and 112 have the thickness 113, as defined by the number of sub-group paper sheets in the pads 111 and 112.

Fundamentally, the pair of flat folded pleats 19 and 20 formed of the central pad area 17 of diaper 10, the pair of free-standing pleats 53 and 54 formed of the central pad area 55 of diaper 50, and the pair of flat-folded pleats 82 and 83 formed of the central pad area 81 of diaper 80, are all pleats providing channeled urine traps having a pair of dikes or retaining walls for the respective central pad channel widths 28, 52 and 108. The retention of excreted infant urine, and feces as well, is thus provided by channel widths 28, 52, and 108 in the respective diapers 10, 50 and 80.

Since the absorbtion of urine by the absorbent wood pulp paper sheets is not instantaneous, it is quite important to physically control the hydraulic flow of urine for a few seconds while the urine is being absorbed by the wood pulp. It is advantageous to dispose the greater proportion of the absorbent wood pulp of the absorbent pad in the central optimum pad area, and to specifically dispose the absorbent wood pulp in the central pad channel width. The urine normally excreted within the central pad channel width, is then absorbed by the wood pulp disposed in the central channel pad area.

The pairs of narrow flat-folded pleats 19, 20 and 82, 83, and the like, can range in their respective widths 29, 30 and 109, 110, and the like, substantially from approximately one-quarter to one inch width. The free standing pair of pleats 53 and 54 can have pleat side width values 62 and 63 ranging substantially from one-eighth to three-eighths inch.

The fragmentary sectional view of FIG. 5 illustrates the further modification of diaper 10 into diaper 10' wherein the abosrbent pad has a central pad thickness 22'. Thickness 22' is increased over the initial pad thickness 22 by the imbibing of urine fluids and the like. The pleats 19, 20 of diaper 10 raise slightly, forming pleats 19' and 20' on absorbing of urine, and the central pad thickness 22 swells slightly to 22', wherever the infant wearing the diaper does not physically compress the diaper absorbent pad, utilizing the infant's body weight.

The fragmentary sectional detail 6 of FIG. 2 is shown enlarged in FIG. 6. The flat-folded pleat 19 is formed of the central optimum pad area 17, and the pleat apex 24, and the pleat base fold 25 are shown oppositely disposed in the pleat 19. The side width values 34 and 35 of the pleat 19 are formed of the pleat fold. The detailed view illustrates that the terminus 120 of paper sheets forms plural sub-groups of paper sheets as taught in U.S. Pat. No. 3,765,418, and also provide a terminus structure for the sub-group longitudinal margin 16.

In a further modification of my invention, the absorbent pad thickness 23 of border width values 32 and 33 can be equivalent in thickness to central pad thickness 22, thus modifying diaper 10. Likewise, the adsorbent pad thickness 57 of border pad width values 60 and 61 can be equal to central pad thickness 56. Further, the absorbent pad thickness 113 of border pad width values 95 and 96 can be equal to central pad thickness 85.

The pair of pleats provide an equivalent pair of stress expansion joints in each diaper. Thus there is a much smaller probability of splitting of the fluid pervious cover sheet or the layers of absorbent paper sheeting in the pad during the wearing of the diaper by a physically active infant.

The inventive advance disclosed herein teaches the permanent disposition of a pair of parallel pleats in or adjacent to a central pad area, the pleat pair being disposed a substantial distance apart along the full diaper length. The teaching provides a central excreta channel pad area along the full diaper length which can contain and control the flow of body wastes excreted by the infant wearing the diaper. The permanent central channel is provided in the absorbent pad, and the permanent central channel is structurally specifically excluded from the flat configuration of the fluid impermeable membrane which provides the exterior face of the disposable diaper. Therefore, the permanent channel controlling the excreta flow cannot be destroyed by accidentally pulling out or stretching the pleats by the person fitting the diaper on the infant wearer. The pair of pleats forming the permanent control excreta channel area are provided in a rectangular area diaper, allowing the diaper to be fully wrapped and fully fitted around the torso and thighs of the infant wearer in a well known conventional manner. By fully wrapping and fitting a full size rectangular absorbent pad around the infant wearer, the portion of the absorbent pad wrapped around the infant thighs can contain the urine and feces which may escape containment in the excreta central channel pad area. Thus, the excreta central channel pad area of the diaper provides improved containment of infant excreta, preventing soiling of the crib sheets, blankets and other clothes worn by the infant diaper wearer.

In another modification of this invention, a ply of fluid absorbent cellulosic pad area, equivalent in area to the central optimum pad area is coplanarly disposed adjacent to and is a part of said central pad area. The cellulosic central optimum pad area can be selected from the group consisting of fluffed wood pulp and cellulose absorbent paper sheeting. The fluffed wood pulp is the desired fiber density provided by comminuting bleached wood pulp sheeting, such as alpha cellulose sheeting or the like.

The rectangular size of the diaper can be the required dimensions. The number of plies of absorbent wood pulp sheets can be the values required for absorbtion of the infant urine and containment of fluid feces excreta.

Many modifications in the diaper can be made in the light of my teaching. It is understood that within the scope of the claims the invention can be practiced otherwise than as described.

I claim:

1. An infant diaper having a rectangular, coplanar multiple ply, marginally aligned fluid absorbent paper sheet pad area, said pad area having a pair of longitudinal diaper pad exterior margins oppositely disposed to each other, a central longitudinal diaper pad axis, and a diaper total pad width axis normal to said longitudinal diaper pad axis, wherein the improvement combination comprises:
   a fluid absorbent paper sheet pad area having each one of two longitudinal pad margins coincident with one longitudinal diaper pad margin, said pad area having the required thickness;
   a pair of narrow pad pleats oppositely disposed in parrallel along the full longitudinal diaper axis length, each one of said pair of pad pleats formed on a first face of said paper pad area a spaced distance apart, said pair of pleats and the spaced pad area between said pleats together providing an excreta channel pad area, and the diaper total pad width axis value having the value of the second face width of said absorbent pad area excluding the side width values of the pair of narrow pleats;
   a thin, flexible, fluid impermeable membrane disposed adjacently coextensive with the diaper total pad width value, said second face of said absorbent pad area opposite said pad first face, said membrane also forming each one of a pair of opposed longitudinal border seals disposed on said pair of longitudinal diaper pad margins, said seals securing said diaper pad margins.

2. In the combination set forth in claim 1, the further modification wherein the pair of narrow pad pleats have side width values ranging from one-quarter to one inch.

3. In the combination set forth in claim 2, the further modification wherein the pair of pleat apexes are disposed nearer said central longitudinal diaper pad axis than the corresponding pair of pleat base folds.

4. In the combination set forth in claim 2, the further modification wherein the pair of pleat apexes are disposed further from said central longitudinal diaper pad axis than the corresponding pair of pleat base folds.

5. An infant diaper having a rectangular, coplanar multiple ply, marginally aligned fluid absorbent paper sheet pad area, said pad area having a pair of longitudinal diaper pad exterior margins oppositely disposed to each other, a central longitudinal diaper pad axis, and a diaper total pad width axis normal to said longitudinal diaper pad axis, wherein the improvement combination comprises:

at least two sub-groups of marginally aligned, fluid absorbent paper sheet pad areas, each consecutive one of said sub-group pad areas having one longitudinal margin alternatively coincident with one longitudinal diaper exterior margin, each one of said sub-group pad areas providing a substantial overlap width on the serially subsequent sub-group, providing a central optimum pad area having the required multiplicity of fluid absorbent paper sheets:

a pair of narrow width pad pleats disposed parallel along the full longitudinal diaper axis length, each one of said pair of pad pleats formed of said central optimum pad area and disposed on the first face of said central optimum pad area adjacent to the longitudinal exterior margin of said central optimum pad area, a major proportion of said central optimum pad width being free of coverage by said pair of narrow pleats, and the diaper total pad width axis value being equivalent to the width of the second face of said absorbent pad area, excluding the side width values of the pair of narrow width pleat sides, said pair of narrow pleats and the spaced optimum pad area between said pleats together providing an excreta channel pad area; and, a thin, flexible, fluid impermeable membrane disposed adjacent to the diaper total pad width and disposed coextensive with the second face of said absorbent pad area, and said membrane also forming each one of a pair of opposed longitudinal border seals disposed on said pair of longitudinal diaper pad exterior margins.

6. In the combination set forth in claim 5, the further modification wherein the pair of narrow pad pleats have side width values ranging from one quarter to one inch.

7. In the combination set forth in claim 6, the further modification wherein the pair of pleat apexes are disposed nearer said central longitudinal diaper pad axis than the corresponding pair of pleat base folds.

8. In the combination set forth in claim 6, the further modification wherein the pair of pleat apexes are disposed further from said central longitudinal diaper pad axis than the corresponding pair of pleat base folds.

9. An infant diaper having a rectangular, coplanar multiple ply, marginally aligned fluid absorbent paper sheet pad area, said pad area having a pair of longitudinal diaper pad exterior margins oppositely disposed to each other, a central longitudinal diaper pad axis, and a diaper total pad width axis normal to said longitudinal diaper pad axis, wherein the improvement combination comprises:

at least two sub-groups of marginally aligned, fluid absorbent paper sheet pad areas, each consecutive one of said sub-group pad areas having one longitudinal margin alternatively coincident with one longitudinal diaper pad exterior margin, each one of said sub-group pad areas providing a substantial overlap width on the serial subsequent sub-groups, a first said sub-group having a margin co-aligned with a first said longitudinal diaper pad exterior margin, and a second subgroup having a margin co-aligned with the second longitudinal diaper pad exterior margin opposed to said first longitudinal exterior margin, forming a second sub-group overlap on a first sub-group, providing a central optimum pad area having a multiplicity of fluid absorbent tissue paper sheets;

at least one ply of fluid absorbent cellulosic pad area, equivalent in area to said central optimum pad area and disposed coplanarly coextensive with said central optimum pad area, said cellulosic pad area selected from the group consisting of fluffed wood pulp and cellulose paper sheeting;

a pair of narrow pad pleats disposed parallel and free standing along the longitudinal diaper axis length, each one of said pair of pad pleats formed of said central optimum pad area and disposed on the first face of said central optimum pad area adjacent to the longitudinal exterior margin of said central optimum pad area, and the diaper total pad width axis value having the value of the second face width of said absorbent pad area excluding the side width values of said pair of low-height pleats, said pair of narrow pad pleats and the spaced optimum pad area between said pleats together providing an excreta channel pad area; and, a thin, flexible, fluid impermeable membrane disposed adjacent to the diaper total pad width and disposed coextensive with the second face of said absorbent pad area, and said membrane forming each one of a pair of opposed longitudinal border seals disposed on said pair of longitudinal diaper pad exterior margins.

10. In the combination set forth in claim 9, the further modification wherein the pair of narrow pad pleats have side width values ranging from one-quarter to one inch.

11. In the combination set forth in claim 10, the further modification wherein the pair of pleat apexes are disposed nearer said central longitudinal diaper pad axis than the corresponding pair of pleat base folds.

12. In the combination set forth in claim 10, the further modification wherein the pair of pleat apexes are disposed further from said central longitudinal diaper pad axis than the corresponding pair of pleat base folds.

* * * * *